(12) United States Patent
Klotz

(10) Patent No.: US 11,577,935 B2
(45) Date of Patent: Feb. 14, 2023

(54) ASCENSION AID FOR A WIND TURBINE

(71) Applicant: Wobben Properties GmbH, Aurich (DE)

(72) Inventor: Thomas Klotz, Schönebeck (DE)

(73) Assignee: Wobben Properties GmbH, Aurich (DE)

( * ) Notice: Subject to any disclaimer, the term of this patent is extended or adjusted under 35 U.S.C. 154(b) by 98 days.

(21) Appl. No.: 16/766,143

(22) PCT Filed: Dec. 6, 2018

(86) PCT No.: PCT/EP2018/083859
§ 371 (c)(1),
(2) Date: May 21, 2020

(87) PCT Pub. No.: WO2019/115360
PCT Pub. Date: Jun. 20, 2019

(65) Prior Publication Data
US 2020/0361746 A1 Nov. 19, 2020

(30) Foreign Application Priority Data
Dec. 11, 2017 (DE) .................... 10 2017 129 372.8

(51) Int. Cl.
*B66B 5/24* (2006.01)
*F03D 80/00* (2016.01)
(Continued)

(52) U.S. Cl.
CPC .............. *B66B 5/24* (2013.01); *B66B 5/0093* (2013.01); *B66B 5/027* (2013.01); *F03D 80/00* (2016.05)

(58) Field of Classification Search
CPC ........ B66B 7/1223; B66B 5/24; B66B 5/0093
See application file for complete search history.

(56) References Cited

U.S. PATENT DOCUMENTS 4,106,753 A * 8/1978 Cavalieri ................. B66D 1/54
188/188
7,377,371 B2 5/2008 Reuter et al.
(Continued)

FOREIGN PATENT DOCUMENTS

DE 490091 C 1/1930
DE 1233551 B 2/1967
(Continued)

OTHER PUBLICATIONS

"Amendment to Avanti Service Lift, Model Shark", Dec. 22, 2016, retrieved from http://www.avanti-online.com/downloads/english, p. 3—col. 2, (4 pages).

*Primary Examiner* — Diem M Tran
(74) *Attorney, Agent, or Firm* — Seed Intellectual Property Law Group LLP

(57) ABSTRACT

There is provided an ascension aid for a wind turbine comprising a cabin, a catch unit which co-operates with a securing cable as a securing means and a testing unit for testing the functionality of the catch unit. The testing unit has a base plate, a closure counterpart holder, a closing member and an actuating element coupled to the closing member. By actuation of the actuating element the closing member and the closure counterpart holder clamp the securing cable and the closing member and the closure counterpart holder move upwardly along the base plate. Upon release or de-activation of the actuating element the closing member releases the securing cable and the catch unit trips.

12 Claims, 6 Drawing Sheets

(51) Int. Cl.
*B66B 5/00* (2006.01)
*B66B 5/02* (2006.01)

(56) References Cited

U.S. PATENT DOCUMENTS

| | | | |
|---|---|---|---|
| 9,415,973 | B2 | 8/2016 | Rottlaender et al. |
| 10,519,005 | B2 * | 12/2019 | Rivero .................... B66B 5/044 |
| 10,626,851 | B2 * | 4/2020 | Munk-Hansen ........ F03D 80/50 |

FOREIGN PATENT DOCUMENTS

| | | |
|---|---|---|
| DE | 10334654 A1 | 2/2005 |
| DE | 102016109859 A1 | 11/2017 |
| EP | 3181503 A1 | 6/2017 |
| GB | 2263681 A | 8/1993 |
| JP | H04341476 A | 11/1992 |
| JP | 2006143341 A | 6/2006 |
| JP | 2014-523381 A | 9/2014 |
| WO | 2019/034720 A1 | 2/2019 |

* cited by examiner

ASCENSION AID FOR A WIND TURBINE

BACKGROUND

Technical Field

The present invention concerns an ascension aid for a wind turbine, a wind turbine and a method of testing a wind turbine ascension aid.

Description of the Related Art

An ascension aid, for example, in the form of an elevator, is typically provided in the interior of a tower of the wind turbine so that the service personnel can gain access upwardly into the pod. In addition material and components of the wind turbine can be transported upwardly by means of the ascension aid.

The ascension aid is typically moved up and down by means of a travel cable. A catch device is typically provided as a safety measure, the catch device then engaging, for example, into a redundant safety cable if the ascension aid moves unexpectedly downwardly.

Before an ascension aid is used by the service personnel the procedure for safety-related reasons is to check the function of the catch device. That is typically carried out by manual actuation of the securing cable. As the securing cable including the catch device is however provided on the roof of the ascension aid manual checking of that kind can only be carried out with great difficulty.

On the German patent application from which priority is claimed the German Patent and Trade Mark Office searched the following documents: DE 103 34 654 A1, DE 490 091 A, GB 2 263 681 A and EP 3 181 503 A1.

BRIEF SUMMARY

Provided is an ascension aid for a wind turbine, which permits improved checking of the catch device.

Thus there is provided an ascension aid for a wind turbine, which has a cabin, a catch unit which co-operates with a securing cable as a securing means and is adapted to prevent the cabin moving unexpectedly downwardly, and a testing unit for testing the functionality of the catch unit. The testing unit has a guide unit for the securing cable and an entrainment unit for the securing cable. The entrainment unit is suitable for pulling the securing cable upwardly. The securing cable is pulled upwardly by actuation of the entrainment unit, and that can result in the catch unit tripping. By actuation of the entrainment unit and by pulling the securing cable upwardly it is thus possible to simulate a dropping movement of the ascension aid to be able to test the functionality of the catch unit. The faster the entrainment unit and therewith the securing cable are pulled upwardly the correspondingly faster is the simulated drop of the ascension aid.

According to an aspect of the present invention the guide unit has a base plate. The entrainment unit has a closure counterpart holder and a closing member. The testing unit can further have an actuating element coupled to the closing member.

According to a further aspect of the present invention the securing cable can be clamped by actuation of the actuating element by means of the closing member and the closure counterpart holder and moved upwardly along the base plate together with the closing member and the closure counterpart holder.

According to a further aspect of the present invention the catch unit trips upon actuation of the actuating element.

According to a further aspect of the present invention the closing member releases the securing cable when the actuating element is released or de-activated.

Thus there is provided a wind turbine ascension aid comprising a cabin, a catch unit which co-operates with a securing cable as a securing means and a testing unit for testing the functionality of the catch unit. The testing unit has a base plate, a closure counterpart holder, a closing member and an actuating element coupled to the closing member. By actuation of the actuating element the closing member and the closure counterpart holder clamp the securing cable and the closing member and the closure counterpart holder move upwardly along the base plate. Upon release or de-activation of the actuating element the closing member releases the securing cable. The catch unit can already trip upon actuation of the actuating element on the travel distance P in the testing unit.

According to an aspect of the present invention the actuating element is in the form of a cable pull. The closing member is coupled to an end of the cable pull and a second end of the cable pull extends into the cabin. By actuation of the cable pull the closing member and the closure counterpart holder clamp the securing cable and the closing member and the closure counterpart holder are moved upwardly along the base plate. The catch unit can trip upon actuation of the cable pull. When the cable pull is released the closing member releases the securing cable.

According to an aspect of the present invention the base plate has at least one slot. The closing member and the closure counterpart holder are arranged on a slider which is displaceable along the at least one slot upon actuation of the cable pull.

According to a further aspect of the present invention the closing member is coupled to the base plate by way of a torsion spring and the closing member is urged into a starting position.

According to a further aspect of the present invention the actuating element can be in the form of an electrically activatable actuating element with an actuator. The invention also concerns a wind turbine having an ascension aid as described hereinbefore.

The ascension aid typically has a roof on which a catch device is provided. The catch device can engage into a redundant safety cable. There is a testing unit for testing the catch device. That is intended to permit defined testing of the catch device.

Further configurations of the invention are subject-matter of the appendant claims.

BRIEF DESCRIPTION OF THE SEVERAL VIEWS OF THE DRAWINGS

Advantages and embodiments by way of example of the invention are described more fully hereinafter with reference to the drawing.

DETAILED DESCRIPTION

Figure 1:
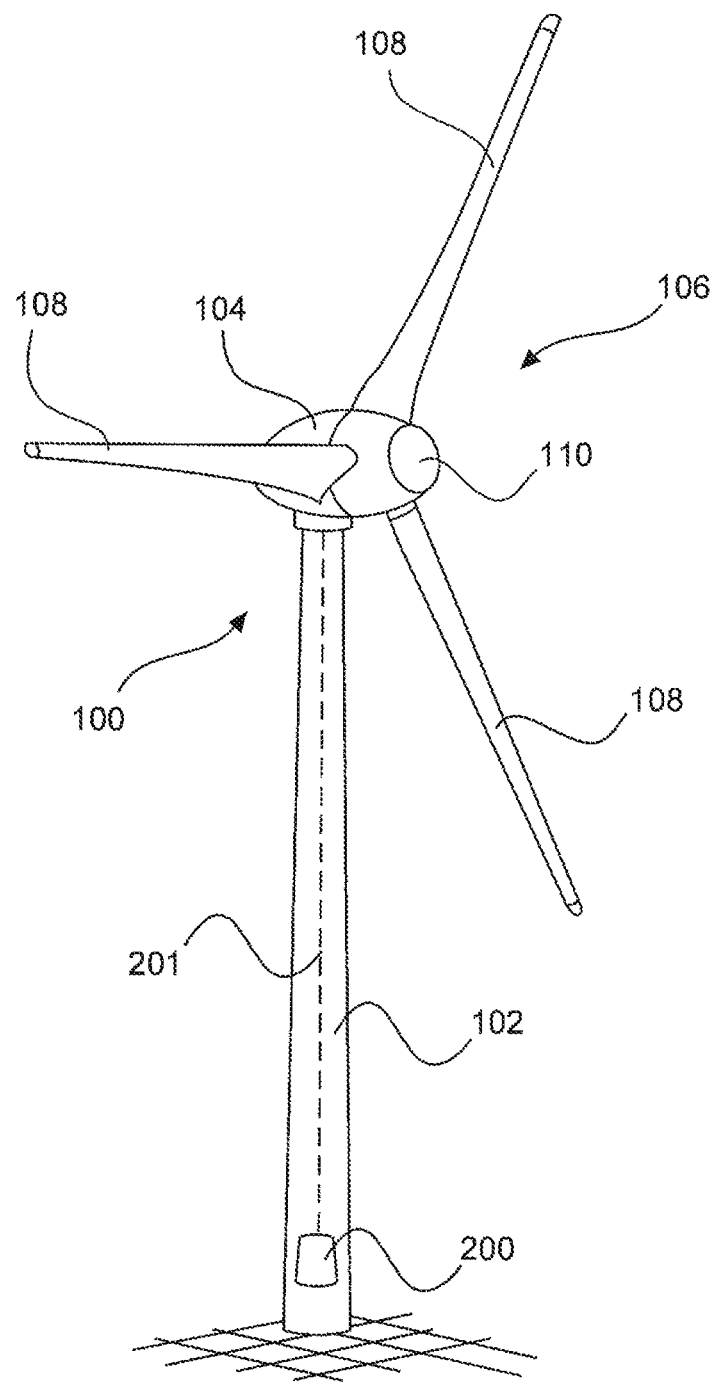
FIG. 1 shows a diagrammatic view of a wind turbine according to the invention.

FIG. 1 shows a diagrammatic view of a wind turbine according to the invention. The wind turbine 100 has a tower 102 with a pod 104 on the tower 102. The pod 104 has an aerodynamic rotor 106 with three rotor blades 108 and a spinner 110. The aerodynamic rotor 106 is coupled to a rotor of a generator (for example, a synchronous generator) so that rotation of the aerodynamic rotor 106 leads to rotation of the rotor of the generator whereby electric power is generated. A pitch angle of the rotor blades 108 can be altered by means of pitch motors at the rotor blade roots.

Provided in the interior of the tower 102 is an ascension aid 200 so that service personnel and components of the wind turbine can be transported from the base of the tower 102 upwardly into the pod 104.

Figure 2:
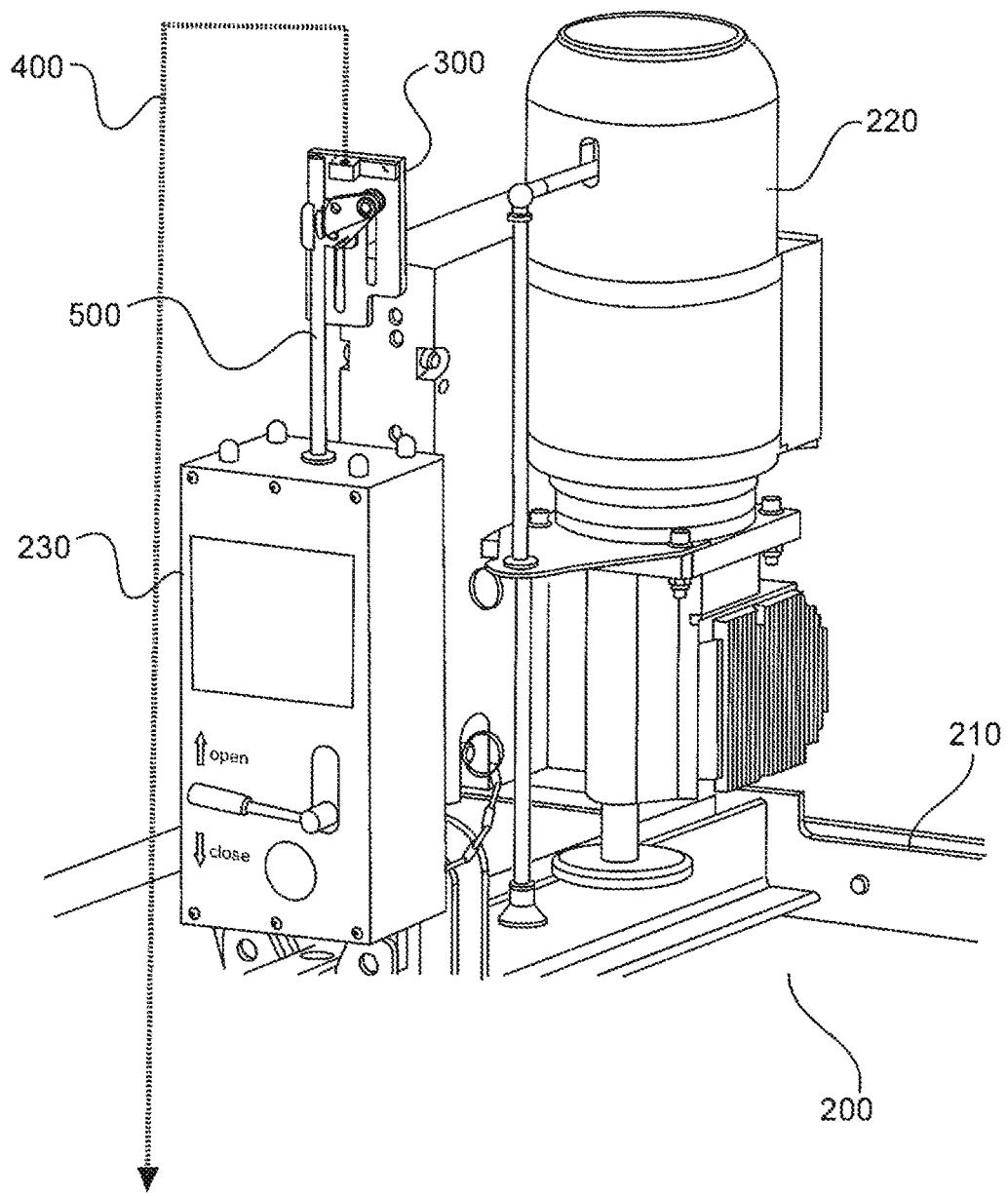
FIG. 2 shows a diagrammatic view of a portion of an ascension aid according to a first embodiment.

FIG. 2 shows a diagrammatic view of a portion of an ascension aid according to a first embodiment. The ascension aid 200 has a basket, cage, frame structure or a cabin 210 and a motor 220, by means of which the ascension aid can be conveyed upwardly or downwardly by way of a travel cable 201. In addition the ascension aid 200 has a catch unit 230 which co-operates with a securing cable 500 and holds the ascension aid 200 on the securing cable 500 if the ascension aid 200 drops down in unplanned fashion. The ascension aid 200 has a testing unit 300 which serves to test the functionality of the catch device 230.

Figure 3:
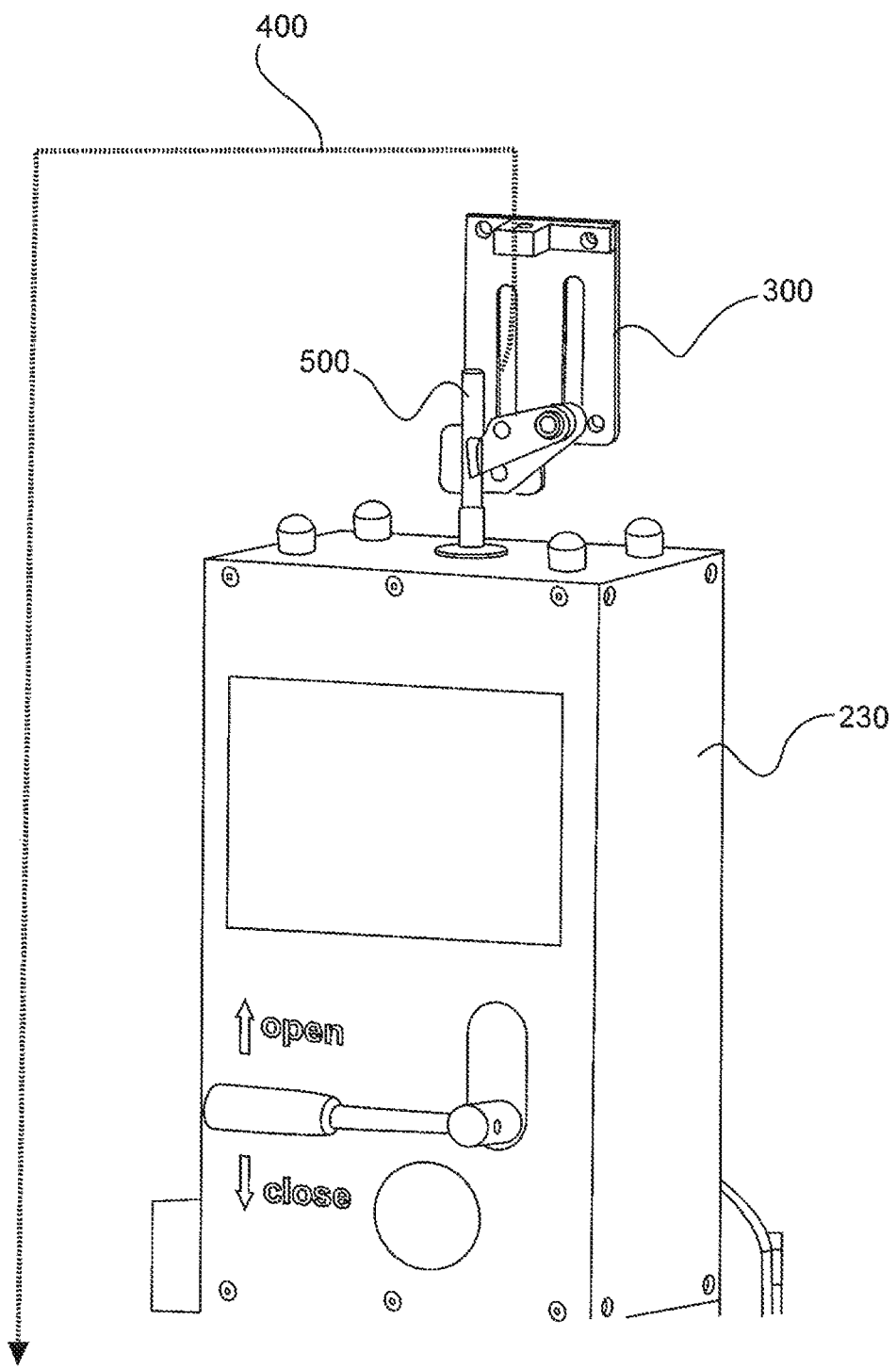
FIG. 3 shows a diagrammatic view of a catch device for an ascension aid according to the first embodiment, and FIGS. 4A-6C each show a diagrammatic view of a testing unit for the catch device according to the first embodiment.

FIG. 3 diagrammatically shows the catch device and the testing unit. The redundant safety cable 500 is coupled to the catch device 230. The testing unit 300 is arranged, for example, above the catch device 300 and accommodates the safety cable 500.

Figure 4A:
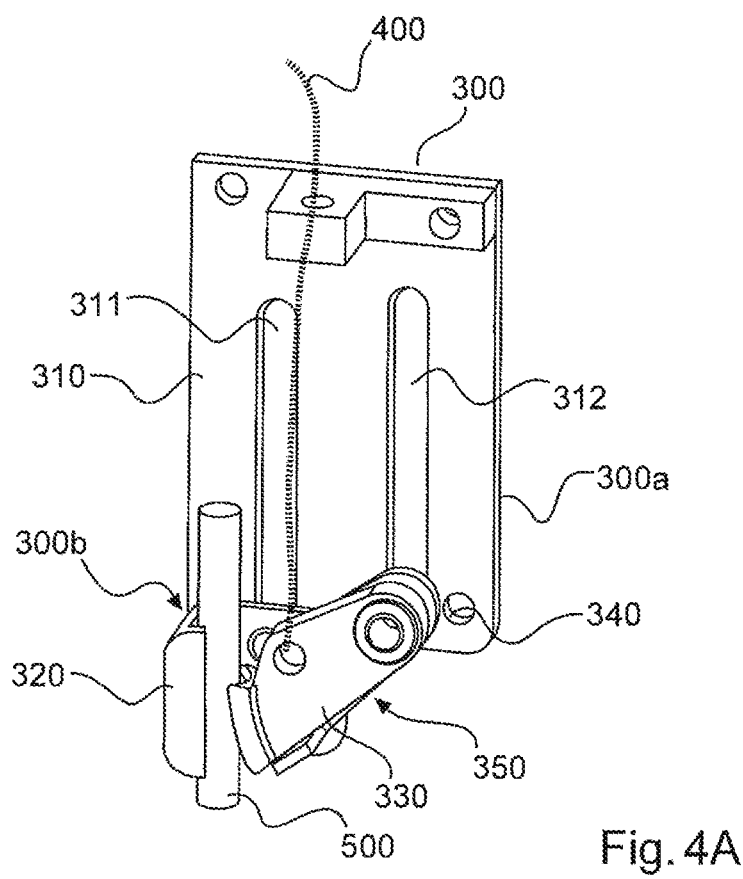
Figure 4B:
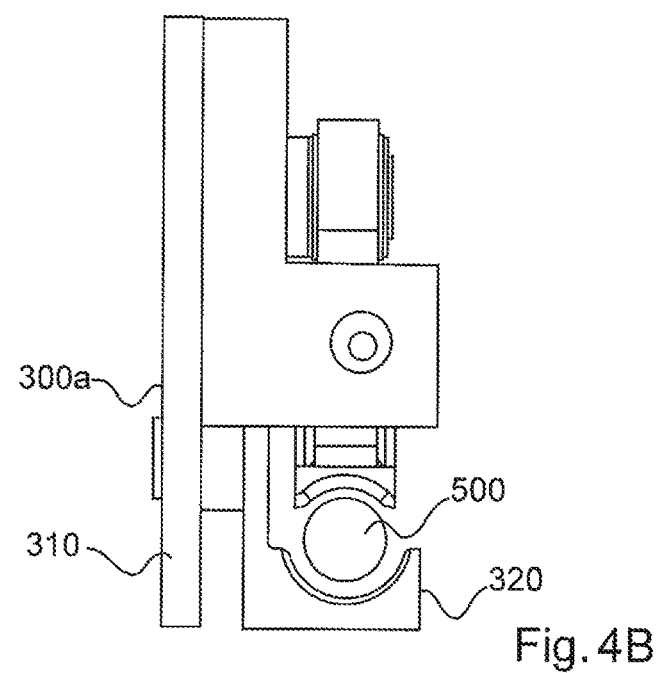
Figure 5A:
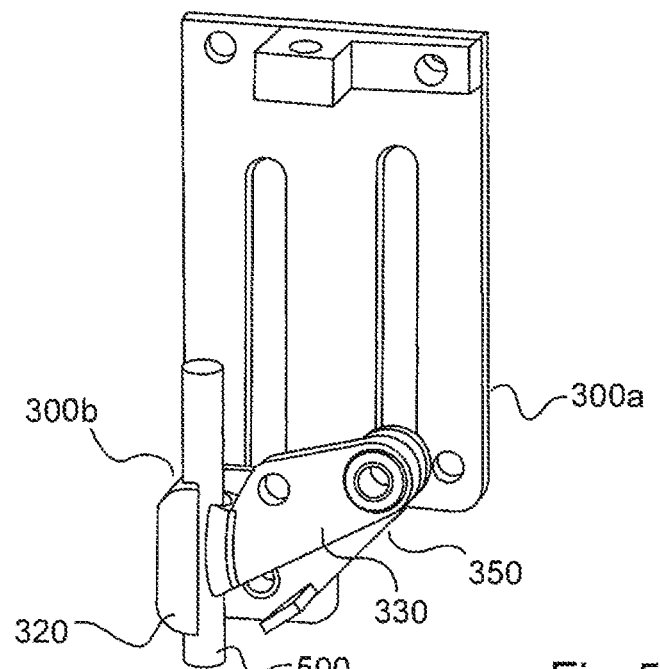
Figure 5B:
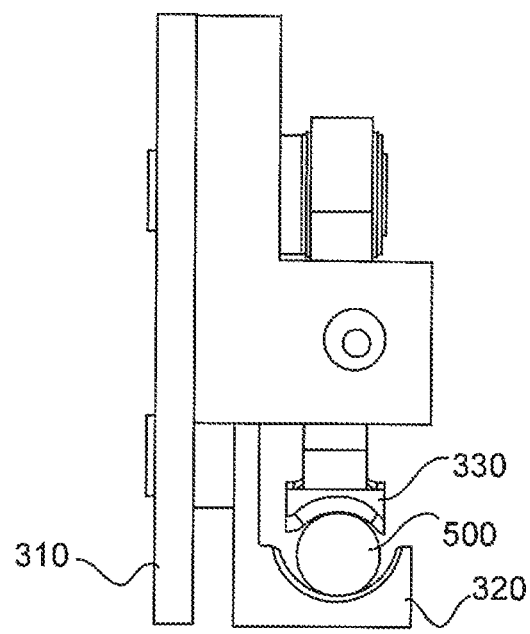
Figure 6C:
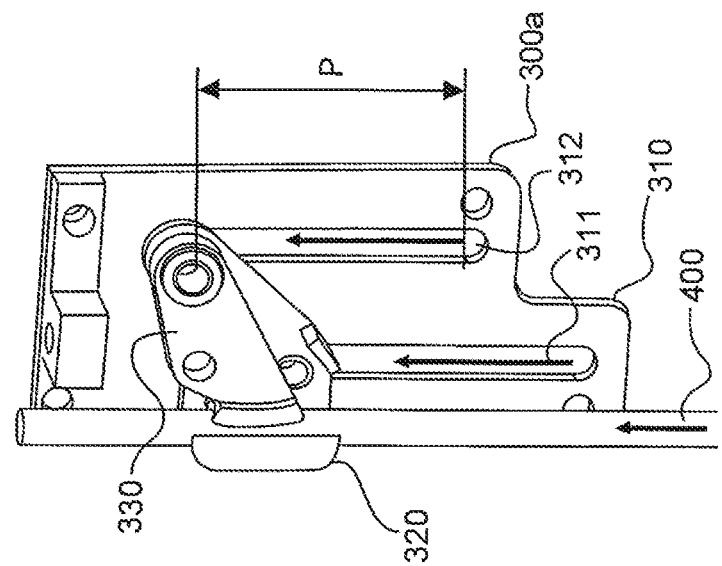
Figure 6B:
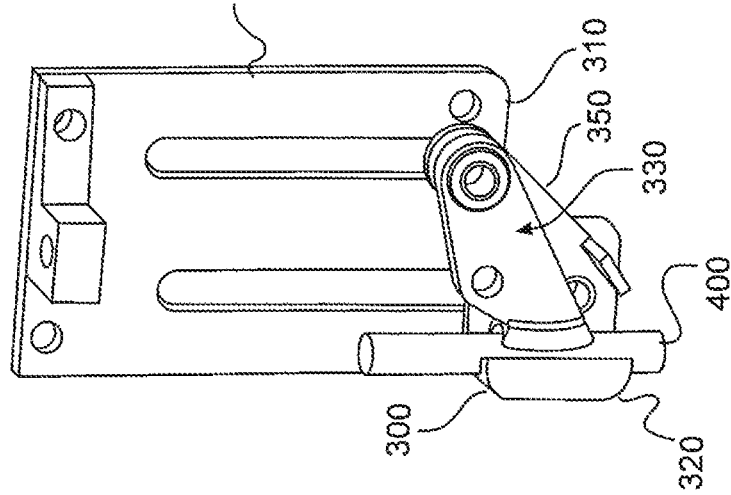
Figure 6A:
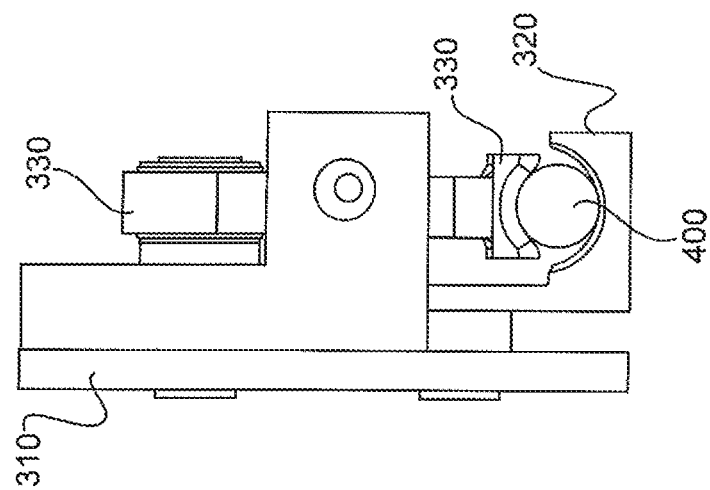

FIGS. 4A to 4C each show a diagrammatic view of a testing unit 300b for the catch device according to the first embodiment. The testing unit 300 has a guide unit 300a having a base plate 310 with two openings or slots 311, 312 and an entrainment unit 300b having a closure counterpart holder 320, a closing member 330 and optionally a torsion spring 340. An actuating element (for example, a cable pull 400) is coupled to the entrainment unit and, for example, the closing member 330.

The entrainment unit 300b (the closure counterpart holder 320 and the closing member 330) can be provided on a slider 350 displaceable along the slots 311, 312.

In the normal travel mode 330 the entrainment unit 300, for example, the closing member 330, is not in contact with the securing cable 500 and the ascension aid 200 can be displaced without impediment upwardly or downwardly within the tower 102.

The base plate 310 of the testing unit 300 is fixedly screwed in or to the ascension aid 200. By actuation of the cable pull 400 the closing member 330 closes against the torsion force of the spring 340 and the securing cable 500 is clamped in the entrainment unit, that is to say between the closure counterpart holder 320 and the closing member 330. Upon further pulling the securing cable 500 can be entrained by the entrainment unit 300b and the entrainment unit of the closure counterpart holder 320 is moved upwardly together with the closing member along the base plate 310. The length of the opening or the slots 311, 312 determines the maximum testing travel distance P. In that case the catch device 230 should trip. The closing member 330 can then be opened again and the closure counterpart holder 320 can move downwardly again into its starting position. That is effected by the closing member 330 being relieved of load indirectly by way of the cable pull 400 and the torsion spring 340 then opening the closing member 330. The cable pull 400 can project into the interior of the ascension aid so that a service operative can actuate the cable pull to check the catch device by means of the testing unit 300.

The closing member 330 is actuated by actuation of the cable pull 400 so that the closing member 330 bears against the safety cable 500. In that case the safety cable 500 is fixed between the closure counterpart holder 320 and the closing member 330. If the cable pull 400 is further actuated then the safety cable 500 (which is fixed between the closure counterpart holder and the closing member) is entrained and the unit comprising the closure counterpart holder and the closing member (namely the slider) is moved upwardly along the slots 311, 312. If that takes place sufficiently quickly the catch device 320 trips before the slider has covered the maximum testing travel distance P. The cable pull can then be moved into its starting position by way of the spring 340 and the slider 350 moves downwardly and the closing member 330 opens so that the safety cable 500 is again free and is no longer fixed. In that way the function of the catch device 300 can be checked by means of the testing unit 300. After unlocking of the catch device 230 the travel mode of the ascension aid 200 can be resumed.

According to an aspect of the present invention the safety cable entrainment can be implemented by way of a closing member, for example, in the form of a conical entrainment member. As an alternative thereto it is possible to provide for electrical tripping.

According to an aspect of the present invention in the case involving electrical tripping it would be possible to set an acceleration value so that the catch device can be checked for all tripping variables.

The invention claimed is:

1. An ascension aid for a wind turbine, comprising:
   a cabin;
   a catch unit that co-operates with a securing cable to secure the cabin and to prevent the cabin from moving unexpectedly downwardly; and
   a testing unit for testing the functionality of the catch unit,
   wherein the testing unit has a guide unit for the securing cable and an entrainment unit for the securing cable,
   wherein the entrainment unit is suitable for pulling the securing cable upwardly,
   wherein the guide unit has a base plate,
   wherein the entrainment unit has a closure counterpart holder, a closing member, an actuating element coupled to the closing member, wherein the actuating element is a cable pull, wherein the closing member is coupled to a first end of the cable pull, wherein a second end of the cable pull extends into the cabin,
   wherein by actuation of the cable pull:
     the closing member and the closure counterpart holder clamp the securing cable, and
     the closing member and the closure counterpart holder are moved upwardly along the base plate,
   wherein the catch unit trips upon actuation of the actuating element, and
   wherein upon release of the cable pull, the closing member releases the securing cable.

2. The ascension aid according to claim 1 wherein by actuation of the actuating element, the closing member and the closure counterpart holder clamp the securing cable, and the closing member and the closure counterpart holder are moved upwardly along the base plate.

3. The ascension aid according to claim 1 wherein the catch unit trips upon actuation of the actuating element.

4. The ascension aid according to claim 3 wherein upon release or de-activation of the actuating element the closing member releases the securing cable.

5. The ascension aid according to claim 1 wherein:
   the base plate has at least one slot, the closing member and the closure counterpart holder are arranged on a slider, and upon actuation of the cable pull, the slider is displaceable along the at least one slot.

6. The ascension aid according to claim 1 wherein the closing member is coupled to the base plate by a torsion spring and urges the closing member into a starting position.

7. An ascension aid for a wind turbine, comprising:

a cabin;

a catch unit that co-operates with a securing cable to secure the cabin and to prevent the cabin from moving unexpectedly downwardly; and a testing unit for testing the functionality of the catch unit, wherein the testing unit has a guide unit for the securing cable and an entrainment unit for the securing cable, wherein the entrainment unit is suitable for pulling the securing cable upwardly, wherein the guide unit has a base plate, wherein the entrainment unit has a closure counterpart holder, a closing member, an actuating element coupled to the closing member, and wherein the actuating element is an electrically activatable actuating element having an actuator.

8. A wind turbine comprising:

a tower; and the ascension aid according to claim 1.

9. A method comprising:

testing the wind turbine ascension aid according to claim 1, the testing comprising:

pulling the securing cable upwardly by the entrainment unit so that the catch unit is tripped.

10. The ascension aid according to claim 7 wherein by actuation of the actuating element, the closing member and the closure counterpart holder clamp the securing cable, and the closing member and the closure counterpart holder are moved upwardly along the base plate.

11. The ascension aid according to claim 7 wherein the catch unit trips upon actuation of the actuating element.

12. The ascension aid according to claim 11 wherein upon release or de-activation of the actuating element the closing member releases the securing cable.

* * * * *